US006198110B1

(12) United States Patent
Kaye et al.

(10) Patent No.: US 6,198,110 B1
(45) Date of Patent: Mar. 6, 2001

(54) METHOD AND APPARATUS FOR THE REAL-TIME CHARACTERIZATION OF PARTICLES SUSPENDED WITHIN A FLUID MEDIUM

(75) Inventors: Paul H Kaye, Kimpton; Edwin Hirst, Hatfield, both of (GB)

(73) Assignee: The Secretary of State for Defence in Her Britannic Majesty's Government of the United Kingdom of Great Britain and Northern Ireland, Farnborough (GB)

( * ) Notice: Subject to any disclaimer, the term of this patent is extended or adjusted under 35 U.S.C. 154(b) by 0 days.

(21) Appl. No.: 09/142,537
(22) PCT Filed: Mar. 27, 1997
(86) PCT No.: PCT/GB97/00871
§ 371 Date: Sep. 8, 1998
§ 102(e) Date: Sep. 8, 1998
(87) PCT Pub. No.: WO97/36165
PCT Pub. Date: Oct. 2, 1997

(30) Foreign Application Priority Data

Mar. 27, 1996 (GB) .................................................. 9606423

(51) Int. Cl.[7] .................................................. G01N 15/06
(52) U.S. Cl. .......................... 250/575; 250/573; 356/336
(58) Field of Search .................................. 250/575, 573, 250/574, 577, 222.2; 356/335, 336, 337, 338, 341, 342, 343

(56) References Cited

U.S. PATENT DOCUMENTS 4,441,816 * 4/1984 Hencken et al. ...................... 356/335
4,957,363 * 9/1990 Takeda et al. ........................ 250/222.2
4,999,513   3/1991 Ito et al. ................................ 250/575

FOREIGN PATENT DOCUMENTS 38 22 310   1/1989 (DE) .

OTHER PUBLICATIONS

Review of Scientific Instruments, vol. 62, No. 11, Nov. 1, 1991, pp. 2751–2764, XP000271069 Steinkamp J A et al: "Improved Multilaser/Multiparameter Flow Cytometer For Analysis and Sorting of Cells and Particles" see p. 2762—p. 2756; Figures 1,5,7.

* cited by examiner

Primary Examiner—Que T. Le
(74) Attorney, Agent, or Firm—Nixon & Vanderhye P.C.

(57) ABSTRACT

This invention describes a method by which microparticles, typically in the size range from 0.3 $\mu$m to 100 $\mu$m, which are carried in a fluid suspension, may be rapidly detected and characterized. The method primarily relates to the measurement of atmospheric particles such as those in clouds or environmental aerosols, but it may be used to measure other forms of particulate suspension wherever the flow of suspension through a defined measurement space can be achieved. The method is based upon a rapid analysis of the spatial laser scattering profile (i.e., the complex manner in which individual particles scatter laser light) recorded from individual particles as they are carried in suspension through a measurement space. Using this method it is possible to differentiate various types of particles based on particle shape and structure, as manifest in characteristics of their individual spatial light scattering patterns. The sizes of spherical particles and the spherical equivalent sizes of non-spherical particles may also be determined, allowing size distribution for each particle type within the suspension to be determined. An implementation of the method for use in an aircraft mounted instrument is described.

13 Claims, 6 Drawing Sheets

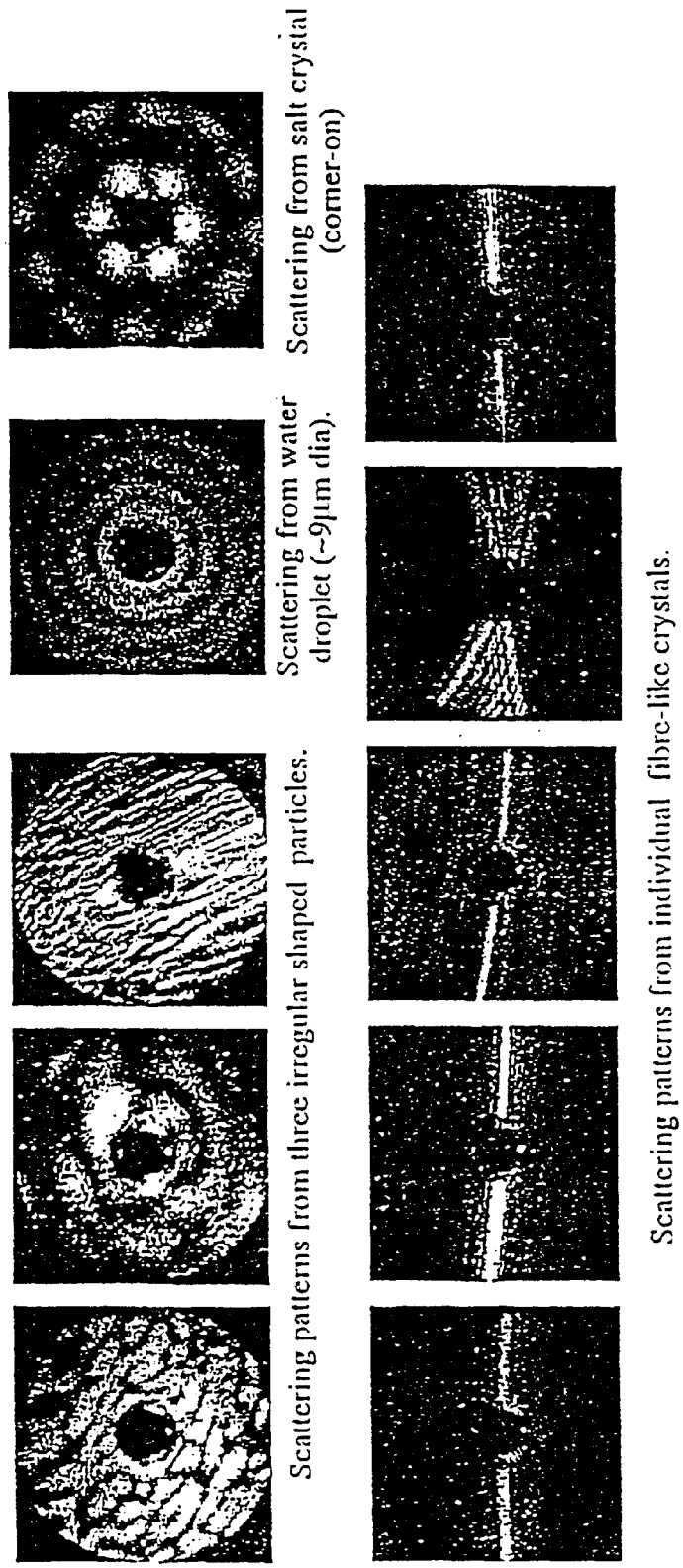

Fig. 1

Examples of transient light scattering patterns from individual airborne particles of various geometries.

The patterns were the result of individual particles passing through a laser beam, and were recorded using a high-speed camera system. The direction of the illuminating beam of light is orthogonal to the Figure and the beam is targeted at the dark beam stop shown at the centre of each pattern.

Examples of Response of Hexagonal Detector Configuration to Various Particle Scattering Events

METHOD AND APPARATUS FOR THE REAL-TIME CHARACTERIZATION OF PARTICLES SUSPENDED WITHIN A FLUID MEDIUM

FIELD OF THE INVENTION

The present invention relates to apparatus for and methods of classifying particle shape in a fluid. It is particularly applicable, but in no way limited to, the real-time classification of particle shape in the atmosphere.

BACKGROUND TO THE INVENTION

In investigations of the composition and dynamics of the earth's particulate atmosphere, particle shape is an important parameter by which classification and possibly identification of particles may often be achieved. Spherical droplets, cuboidal crystals typical of marine aerosols, and the wide variety of morphologies assumed by ice crystals, are examples where the determination of shape may be used in combination with size spectra measurements to provide experimental data upon which theoretical models of macroscopic and microscopic physical behaviour of clouds and aerosols may be developed and tested. A specific example of this involves the study of ice microphysics and the behaviour of droplets and ice crystals which can occur simultaneously within clouds. The radiative properties of these mixed-phase clouds can be radically dependent upon the relative proportions and size spectra of the two phases, as well as the orientations of the ice crystals present, and this has a profound effect upon the proportion of incident sunlight reaching the lower atmosphere and earth surface. To be able to understand the radiative transfer properties of ice and mixed phase clouds, a detailed knowledge of the particles' shapes and sizes is required, along with measurements of the number concentration of ice and super-cooled liquid water particles. Furthermore, measurement of the total ice crystal number is important to facilitate the testing of theories of the nucleation of ice crystals and their role in climate change.

Existing Atmospheric Particle Measurement Techniques

Whilst there are several commercially available aircraft-mounted instruments designed to measure the size spectra of atmospheric particles. The FSSP—Forward Scatter Spectrometer Probe, from Particle Measurement Systems Inc. Boulder Colo.—is perhaps the most widely used in airborne platforms. These instruments cannot provide information relating to particle shape. They are generally calibrated on the assumption that all particles are spherical and they are thus incapable of discriminating between, for example, ice crystals and water droplets of equivalent optical scattering size.

In regard to particle shape measurement, the 2D-OAP-2D—Optical Array Probe from Particle Measurement Systems Inc.—is commonly employed for examining airborne particles greater than ~30 $\mu$m in size. This instrument records a silhouette of individual particles as they pass through a light sheet and occlude elements within a linear detector array arranged orthogonally to the particle trajectory. However, the 2D-OAP suffers a number of limitations, principally:

(i) it provides only limited instantaneous information of the range or distribution of particle sizes within a measured atmosphere (post-processing in the laboratory is normally undertaken to assess shape spectra);

(ii) it suffers from a number of artefacts produced in the recorded data by events such as the collection and subsequent release of liquid water drips from the leading points of the probe arms or the 'splashing' of large droplets on these arms producing artificially high populations of small droplets; and most importantly;

(iii) it cannot accurately resolve the shapes of particles which occlude less than the order of five array pixels, corresponding to particle sizes below about 125 $\mu$m [Moss S. J. and Johnson D. W. Atmospheric Research 34 pp. 1–25, 1994]. The inability to analyze and categorize the shapes of smaller particles makes it impossible for the instrument to differentiate water droplets from ice crystals for these sizes. Therefore the instrument is unable to provide data which can answer the microphysical questions concerning the radiative transfer properties of, for example, cirrus clouds in which the ice particle and water droplet sizes are frequently well below the limit of resolution of the 2D-OAP.

The shapes of smaller particles, theoretically down to ~2–4 $\mu$m but in practice down to ~10 $\mu$m because of aircraft vibration, can be assessed using a holographic technique [Brown, P. R. A. j. Atmos. Oceanic Technol., vol. 6, pp. 293–306, 1989]. This technique involves using a pulsed Nd:YAG laser and photographic film recording system to acquire holographic 'snapshots' of particle populations within a measurement space. The processed holograms are later interrogated using a CW laser to recreate the images of the particles, allowing detailed analysis. This process is extremely slow and manually intensive, taking up to a day for each hologram, and again, the smaller particles of interest are beyond the instrument's limit of resolution.

Spatial Light Scattering Techniques

The applicants have developed several ground-based instruments for the classification and identification of airborne particles by analysis of the manner in which individual particles spatially scatter incident laser illumination. These are described in 'Portable Particle Analysers'. Ludlow, I. K. and Kaye P. H. European Patent EP 0 316 172, July 1992; 'Particle Asymmetry Analyser'. Ludlow, I. K. and Kaye, P. H. European Patent EP 0316 171, September 1992 which represent the closest prior art known to the applicant. In these instruments, airborne particles are drawn from the ambient atmosphere by a suction pump and are constrained by narrow delivery tubes, typically 1 mm in diameter, and a surrounding layer of filtered sheath air, to pass through an incident laser beam within a laser scattering chamber. The intersection of the particle flow with the beam defines the measurement space through which all particles in the sample flow will pass. Particle flow is such that statistically, particle coincidences within the measurement space are rare. Each particle passing through the measurement space will scatter light in a manner which is governed inter alia by the size, shape, and structure of the particle. FIG. 1 shows typical light scattering patterns recorded from individual microscopic airborne particles. The black circle at the centre of each pattern is caused by a beam stop, and the outer circumference of the patterns corresponds to scattering at an angle of approximately 35° to the direction of the incident beam. As can be seen in FIG. 1, spherical particles such as droplets produce a regular concentric ring scattering patterns, whilst elongated particles such as fibres or long crystals produce linear scattering angled according to the orientation of the particle. Irregular shaped particles may produce more complex patterns with few easily discernible features. In the instruments described in the aforementioned prior art, the scattering patterns as shown in FIG. 1 are collected by the three detectors arranged symmetrically about the laser beam axis. By measurement of the difference in magnitude of the signals received from the three detectors, a crude estimate of the shape of the scattering particle may be deduced. However, the type of instrument described above is not suitable for measuring atmospheric particles such as ice crystals or super-cooled water droplets for the following reason: in the measurement of atmospheric particles it is essential that neither the phase (ie: ice or water) nor the orientation (which governs radiative behaviour) of the particles is affected by the measurement process. This precludes the use of a pumped sample delivery system in which the particles are drawn from the atmosphere via narrow tubes into a measurement chamber. Such a pumped system would certainly change the orientation of the particles and would be likely to melt or partially melt smaller ice crystals present in the sample.

With the foregoing argument in mind, the present invention has the objective of providing a means by which the sizes, shapes, and orientations of fluid-borne particles may be determined rapidly and non-intrusively, ie: in a way which will not materially affect the particles under examination. The present invention thus provides improved apparatus and methods for the classification and characterization of the shape of such particles which overcome or mitigate some or all of the above disadvantages.

SUMMARY OF THE INVENTION

According to a first aspect of the present invention there is provided a particle analyzer for use in characterizing the shape of particles in a fluid medium, said particle analyser comprising:

(i) means for providing a sample of fluid in the form of a flow through a scattering chamber;

(ii) means for generating a first beam of radiation having a first wavelength;

(iii) means for generating a second beam of radiation having a second wavelength wherein the first and second wavelengths are different, said first and second beams of radiation being adapted to intersect each other to create a so-called virtual measurement space;

(iv) a first detection means adapted to detect radiation scattered by a particle passing through the first beam of radiation;

(iv) a second detection means adapted to detect radiation scattered by a particle passing through the second beam of radiation;

(vi) means for deriving data from the radiation detected by the respective detection means;

(vii) means for comparing said derived data with data from particles of known shape.

By providing two intersecting beams of radiation, which are preferably laser light, this creates a "virtual" measuring space which avoids the necessity of using narrow delivery tubes. This has the advantage that fluids flowing through large diameter pipes can be sampled for its particle content without disruption of the flow.

Preferably the first beam of radiation has a cross-section which is substantially a narrow ellipse. This presents a relatively thin sheet of light through which the particles pass.

Preferably the second beam of radiation has a cross-section which is substantially circular and the diameter of the second beam of radiation is less than the widest dimension of the first beam.

In a particularly preferred embodiment the first and second beams intersect at an angle of substantially 60°.

Preferably the first detection means comprises a plurality of individual optical detectors. A wide variety of different arrays can be used in order to derive information regarding particle shape.

Preferably the means for deriving data from the radiation is adapted to identify particles which pass through the virtual measurement space and is further adapted to gather and process data from the first detection means specifically derived from particles which pass through the virtual measurement space. This has the advantage that only particles which pass through the virtual measuring space will produce simultaneous scattering from both beams. The scattering pattern derived from only those particles may be collected and processed.

Preferably the first and second detection means comprise a lens system a photodetector, and respectively a first or second optical wavelength filter which allows light from only the first or second beam of radiation to reach the respective photodetectors. This enables the scattered light to be differentiated according to its source.

Preferably an aperture is incorporated in front of the or each detector in order to restrict the field of view of the or each detector to substantially the virtual measurement space, enabling spurious scatter signals to be eliminated or much reduced.

According to a second aspect of the invention there is provided a method of particle analysis including the steps of:

(a) passing a sample of fluid through a scattering chamber;

(b) passing a first beam of radiation having a first wavelength and a second beam of radiation having a second wavelength through the chamber such that the two beams intersect to form a virtual measurement space;

(c) identifying those particles which pass through the virtual measurement space;

(d) detecting and collecting radiation having a first wavelength which is scattered by said particles with a first detection means;

(e) converting the radiation collected into electrical signals (f) processing and analyzing the electrical signals and comparing them with signals from data derived from particles of known shape.

The method and thus protection sought extends to the use of any versions of the apparatus as herein described.

BRIEF DESCRIPTION OF THE DRAWINGS

The invention will be further described, by way of example, with reference to the accompanying drawings in which:

FIG. 1 illustrates typical light scattering patterns from individual particles of various geometries;

DESCRIPTION OF THE PREFERRED EMBODIMENTS

Embodiments of the present invention are now described by way of example only. These examples represent the best ways of putting the invention into practice that are currently known to the Applicant although they are not the only ways in which this could be achieved.

Figure 2:
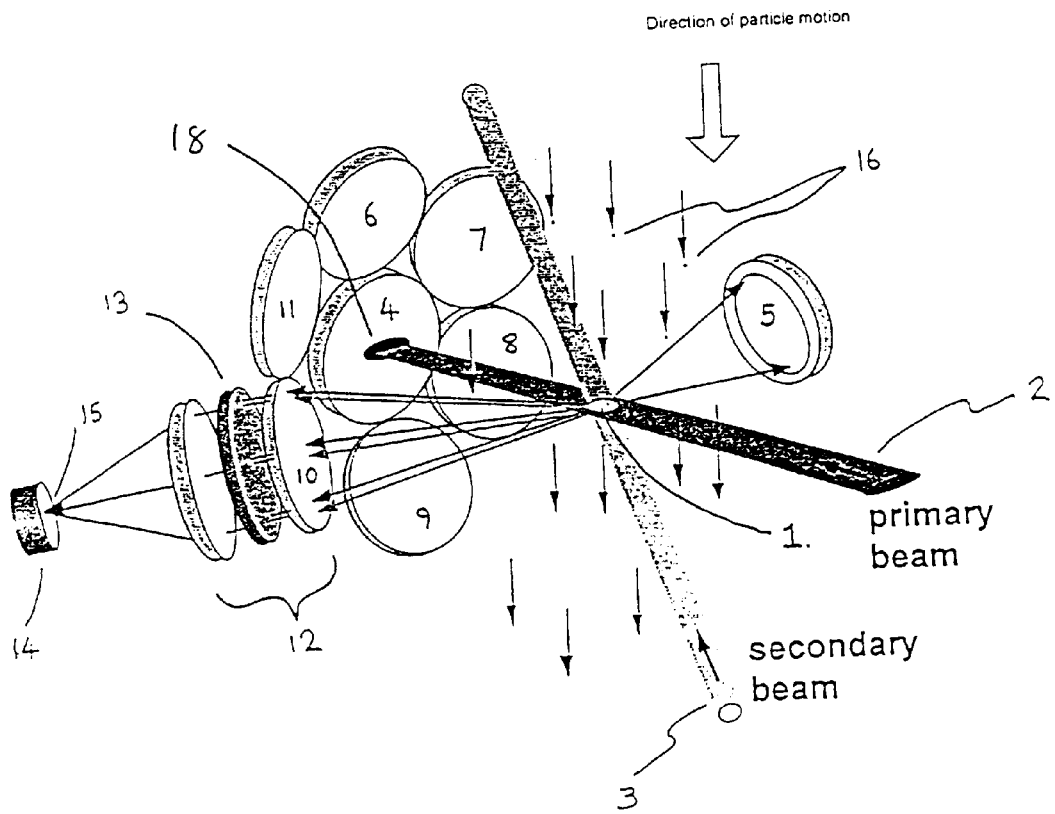
FIG. 2 shows schematically a particle analyzer according to a first aspect of the invention.

The invention is based upon the creation of a virtual measurement space, free from mechanical obstructions and through which particles carried in suspension may pass freely, as shown in FIG. 2. The measurement space 1 is created by the intersection of two laser beams of differing wavelengths, preferably inside a scattering chamber. One beam is referred to as the Primary beam 2, the other beam is referred to as the Secondary beam 3, as shown in FIG. 2. The Primary beam 2 typically has a cross-section which is a narrow ellipse so that it presents a thin sheet of light through which the particle pass. The Secondary beam 3 is typically of a circular cross-section and of a diameter less than the wider dimension of the Primary beam. The angle of intersection of the two beams is typically 60°, such that the measurement space 1 has an approximately circular form, the plane of which is orthogonal to the direction of the particle motion.

Whilst these cross-sections may be preferred they are certainly not the only cross-sections that can be used. Any two beams of radiation of different wavelengths which coincide to produce the virtual measurement space will suffice. The angle of incidence of the two beams is not critical but 60° has been found to work well.

In this context the term scattering chamber has a very broad meaning. It can refer to a defined structure into which fluid flows. Alternatively, it can refer simply to a region within a pipe, tube or duct through which fluid is flowing or able to flow. It therefore need not be a separate, defined structure.

Surrounding the measurement space but at sufficient distance from it to avoid perturbation of the suspended particles is a series of optical detection modules, typically eight in number, and numbered 4 to 11 in FIG. 2. As will be explained, detection modules 4 and 5 are used to establish whether a particle has a 'valid trajectory', ie it passed through the measurement space 1. Detection modules 6 to 11 are then used to assess particle shape and orientation. Each detection module comprises a lens system 12, an optical wavelength filter 13, and a photodetector 14. (For clarity, these items are shown for only one detection module). The lens system of each detection module is arranged such that the field of view of the photodetector is just sufficient to encompass the measurement space 1. This may be achieved by suitably positioning an aperture 15 in front of the photodetector. Particles 16 travel freely through a large volume surrounding the measurement space. This is an important feature of particle analyzers according to this invention. The particle motion relative to the detection modules may be achieved for example by the movement through the cloud or aerosol of interest of an aircraft on which the detection assembly is mounted. Alternatively, the motion of the particles could be caused by their suspension within a gas moving through a large diameter pipe or duct around which are arranged the optical detection modules.

Figure 3:
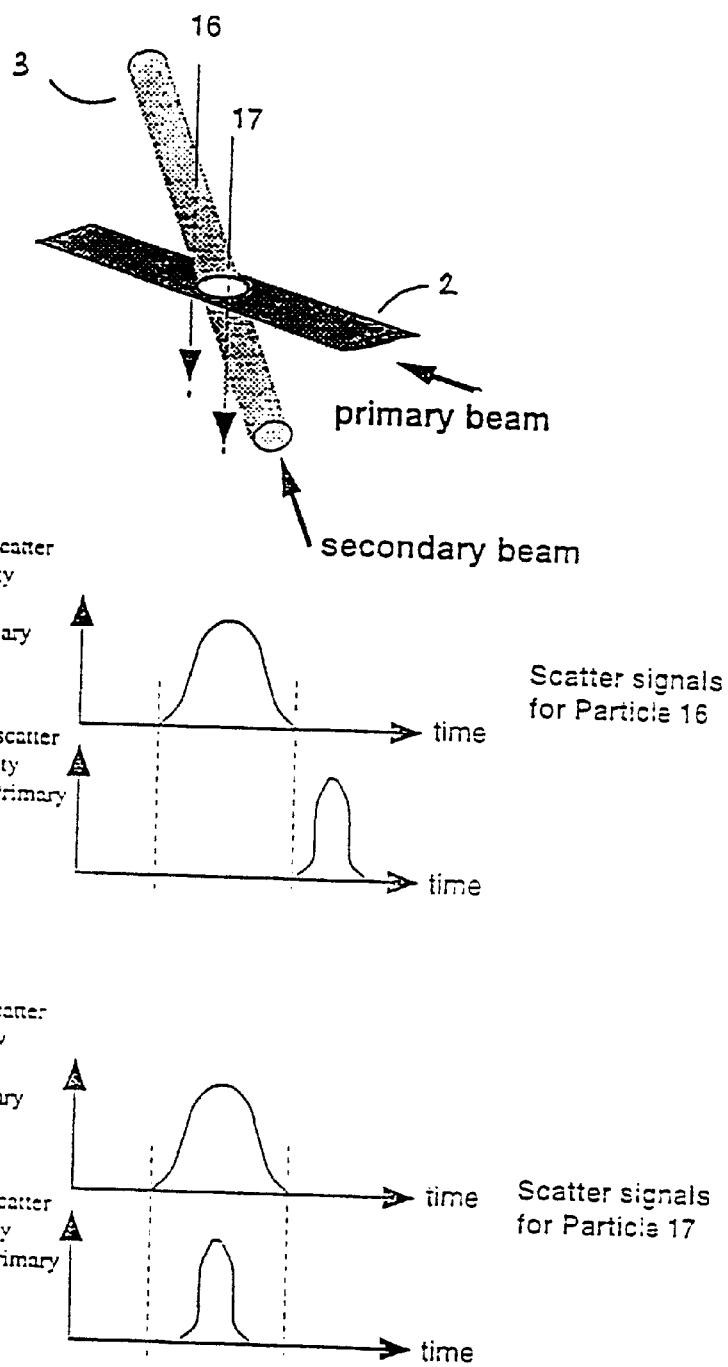
FIG. 3 shows diagramatically light scatter intensity signals produced from particles passing through and adjacent the measurement space of a particle analyzer as illustrated in FIG. 2.

Particles may normally pass through the laser beams at any point along their exposed length and will scatter light in all directions on doing so. However, only particles which pass through the measurement space 1 defined by the intersection of the two beams will produce simultaneous scattering from both beams. This is illustrated in FIG. 3 which shows the timing of electrical pulses from any single photodetector. The traces show the signals resulting from two particles 16 and 17 whose trajectories are close to the measurement space and through the measurement space respectively. For particle 16 the scattered light pulses produced are separated in time as shown in the timing graphs of FIG. 3. For particle 17 the pulses are such that the pulse derived from the Primary beam 2 is always contained entirely within the time duration of that derived form the Secondary beam 3. This is therefore the 'valid trajectory' condition for a particle trajectory through the measurement space.

Referring again to FIG. 2, the optical filter 13 incorporated into the detection module 5 is such that it allows only light from the Secondary beam to pass to its photodetector. The optical filters 13 in all other detection modules are such that they only allow light from the Primary beam to pass to their respective photodetectors. When a particle passes through the measurement space 1 it scatters light in all directions and from both beams simultaneously. The magnitudes of the resulting signals from all detection modules are recorded instantaneously using conventional electronic cicuitry, (not shown). Note that detection module 4 is protected from direct illumination by the Primary beam by a beam stop 18, or a beam dump. Detection module 4 produces an electrical signal caused by the scatter from the particle passing through the Primary beam. Detection module 5 produces an electrical signal caused by the scatter from the particle passing through the Secondary beam. Further electronic circuitry establishes that the 'valid trajectory' condition applies, ie: that the particle has indeed passed through the measurement space. Once this has been established, the magnitudes of the signals from all detection modules are transferred to an electronic processing circuit where an assessment of particle shape and orientation can be made.

Figure 4:
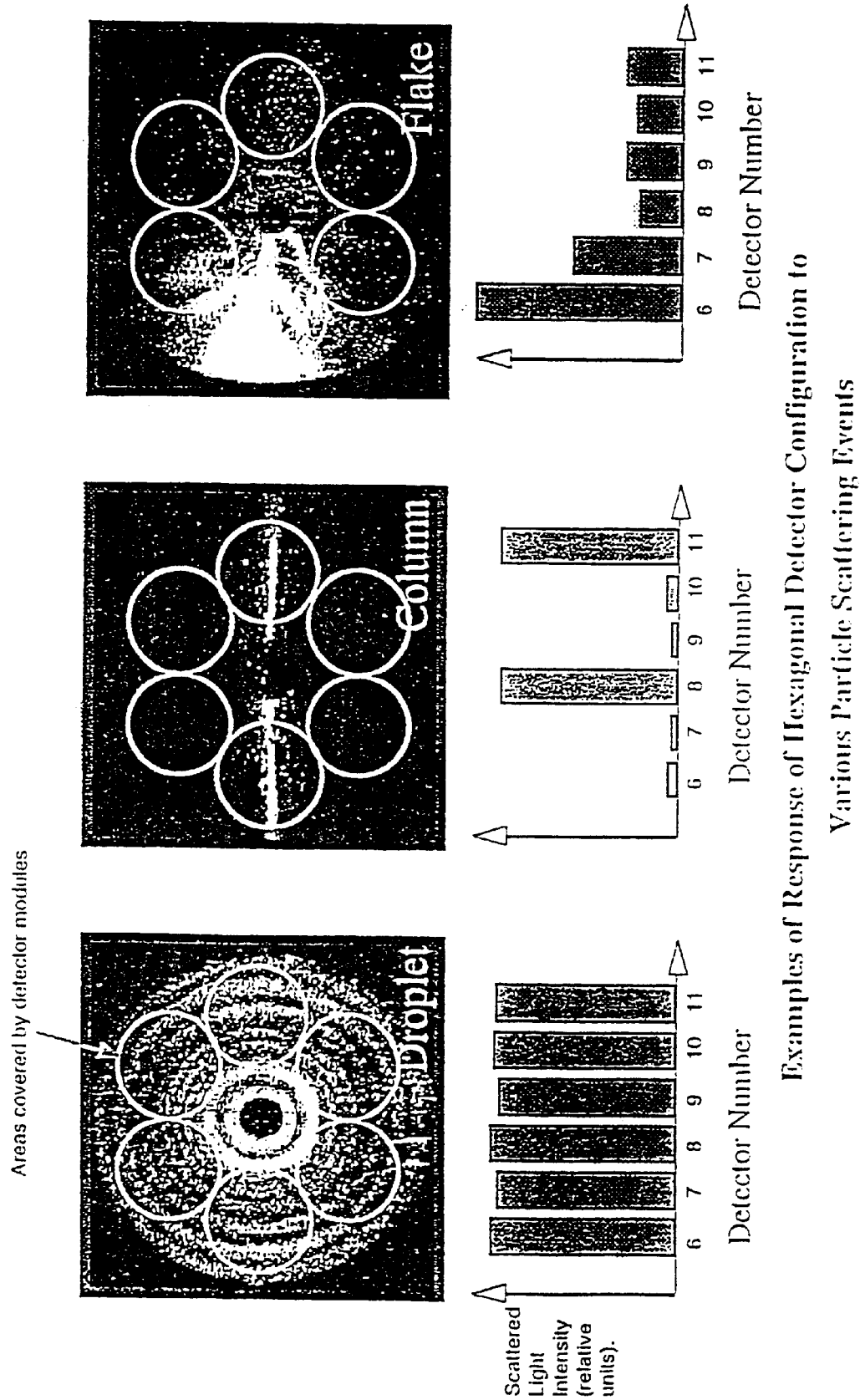
FIG. 4 illustrates examples of the outputs from a six detector array for particles of differing shapes.

FIG. 4 illustrates the derivation of the scatter signals from different particle shapes, a spherical droplet, a columnar particle, and a flake-like particle. The top part of FIG. 4 shows the areas covered by the detector modules 6 to 11 in their hexagonal arrangement superimposed on the typical scattered light patterns from the three types of particle. The graphs underneath each of these examples shows the outputs that would be expected from the detector modules, illustrating how a spherical droplet would yield equal outputs for all six detector modules whilst a columnar particle would yield typically two high and four lower outputs, and a flake would yield a single predominant output.

Figure 5:
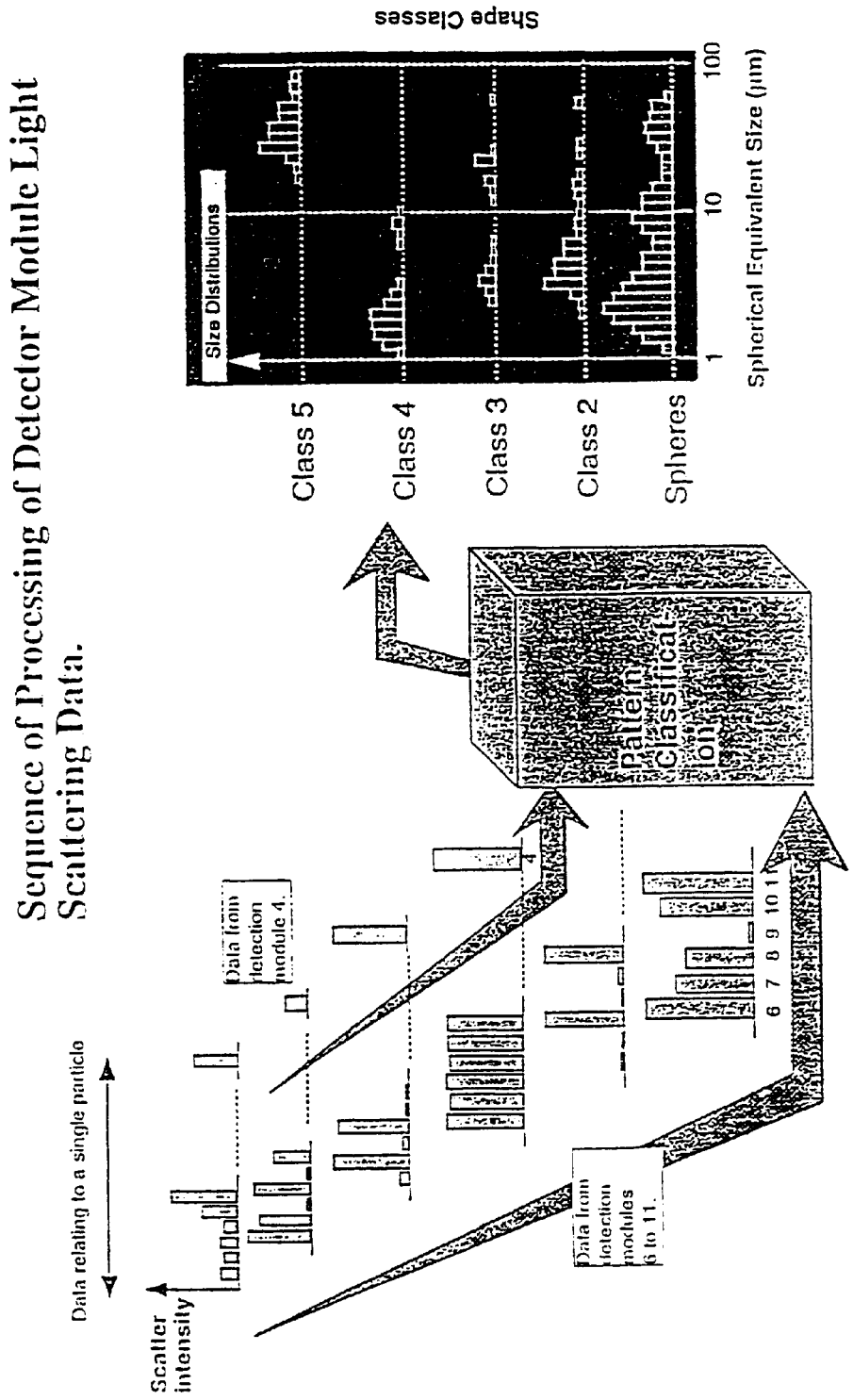
FIG. 5 shows a typical sequence for the processing of detector module light scattering data.

The nature of the processing of the data from the detector modules is illustrated in FIG. 5. The scattered light intensity signal magnitudes from detector 4 and detectors 6 to 11 inclusive are fed into a pattern classification processor. This processor is designed to recognize particular patterns of data and to ascribe the corresponding particle to an appropriate class. The simplest class is that of spherical particles, for which the signals from detectors 6 to 11 should be equal to within instrument measurement accuracy. Other particles, such as elongated crystals, will produce typically two high values in the outputs 6 to 11, with the rest being low. In every case, the signal magnitude from detector 4 is used as a measure of particle size, larger particles generating proportionally higher values. The output of the pattern classification processor may be of the form of a series of size distributions as shown, with spherical particles being one class of particle and other particle shapes (such as column or fibres) being another. There can be as many classes of particle shape as is desired.

The invention may be applied to the measurement and characterization of particles, typically in the range 0.3 μm to 100 μm in size, carried in a fluid medium, either gaseous or liquid wherever the fluid medium is flowing in a direction orthogonal to the plane of the measurement space defined by the intersecting laser beams. The fluid may be travelling along a pipe or tube as may be found in many industrial plant situations, water processing works, etc. In such a case the optical elements of the invention would reside outside the pipe or tube with optical access to the fluid via suitably placed windows in the tube walls.

Figure 6:
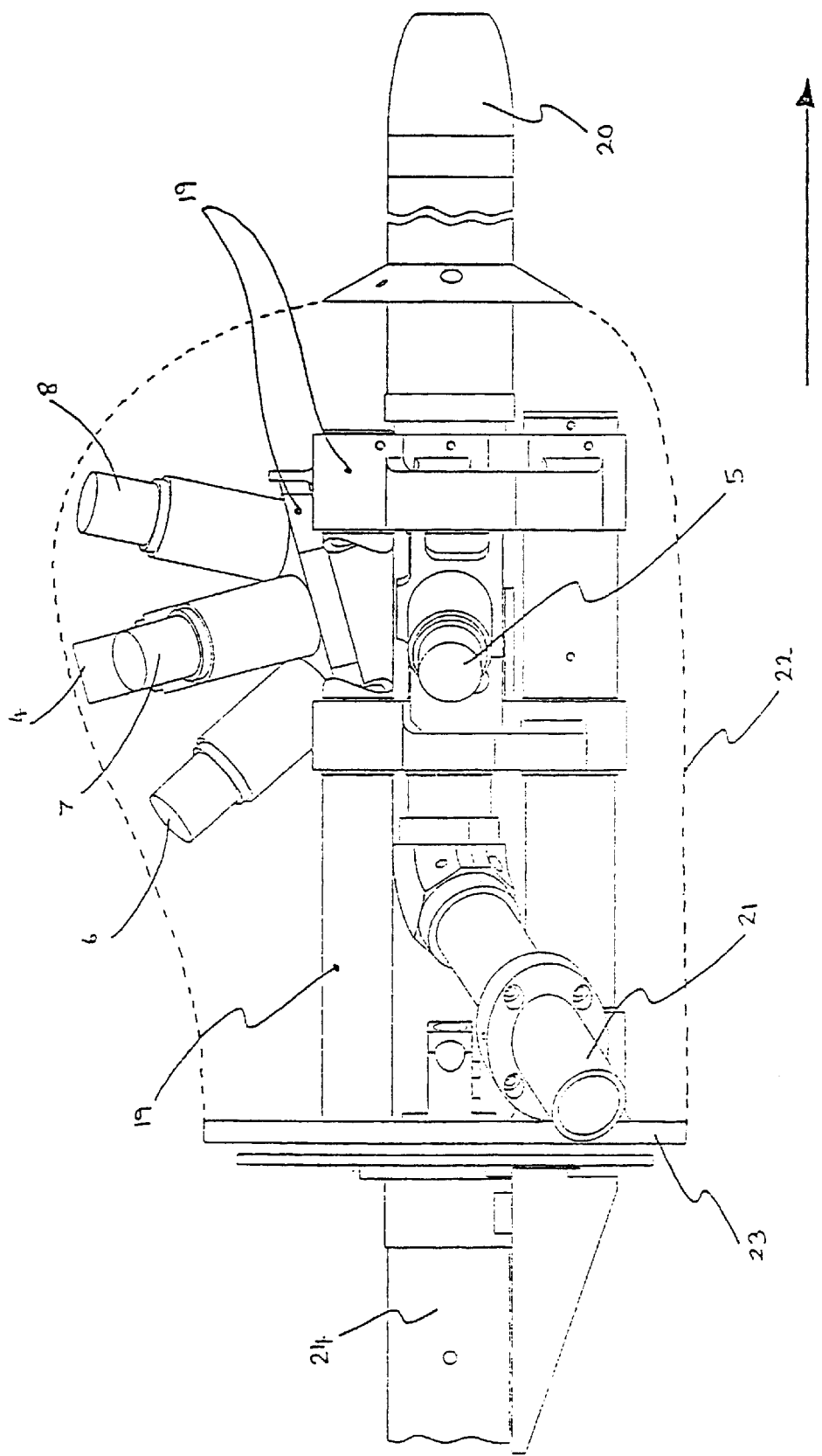
FIG. 6 shows one possible configuration of a particle detector suitable for mounting on an aircraft.

However, a specific embodiment of the invention for use as an aircraft-mounted detector for atmospheric particles is shown schematically in FIG. 6. The detector modules 4, 5, 6, 7 and 8 can be seen supported in a rigid mounting assembly 19. The motion of the aircraft is from left to right as arrowed such that particle laden air (which remains essentially stationary relative to the earth) passes through the intake 20 and out through the vent 21. The internal diameter of the intake is typically 30 mm, sufficient to ensure that particles near the axis of the intake and which will subsequently pass through the measurement space of the instrument are unaffected by the presence of the instrument until after their measurement has taken place. Protecting the optical assembly from the external environment is a shroud 22. Behind the bulkhead 23 are mounted the two lasers 24, together with the data acquisition electronics, the pattern classification processor, and required power supplies. A preferred embodiment of the pattern classification processor is a Radial Basis Function neural network. The Radial Basis Function is arguably one of the simplest forms of artificial neural network, is well documented in pattern classification texts, and may be considered to be prior art. Data from the instrument is fed to an inboard computer via communication data lines carried through the aircraft wing, thus providing the aircraft flight crew with virtually instantaneous data relating to the nature of the particulate cloud through which the aircraft is flying.

What is claimed is:

1. A particle analyzer for use in characterizing the shape of a particle in a fluid medium, said particle analyzer comprising:

means for generating a first beam of radiation, said first beam having a first wavelength;

means for generating a second beam of radiation, said second beam having a second wavelength, said first and second wavelengths being different, said first and second beams intersect each other, said intersection comprising a virtual measurement space, said virtual measurement space located within a flow of said fluid medium and said particle passes through said virtual measurement space without being affected by said flow;

first detection array of detectors for detecting radiation of said first wavelength scattered by said particle passing through said virtual measurement space, each detector providing a first radiation signal responsive to said detected first wavelength radiation at said each detector;

at least one second detector adapted and arranged to detect said second wavelength radiation scattered by said particle passing through said virtual measurement space and provide a second signal responsive to said detected second wavelength radiation; and means for comparing the first and second radiation signals to exclude first radiation signals which are not timewise coincident with second radiation signals and thereby indicating said particle in said virtual measurement space and for comparing said first radiation signals with data from particles of known shape to provide a shape indicative signal for said particle.

2. A particle analyzer as claimed in claim 1 and wherein the first radiation beam has a cross-section which is substantially a narrow ellipse.

3. A particle analyzer as claimed in claim 1 and wherein the second radiation beam has a cross-section which is substantially circular.

4. A particle analyzer as claimed in claim 3 and wherein the diameter of the second radiation beam is less than the widest breadth of the first radiation beam.

5. A particle analyzer as claimed in claim 1 and wherein the first and second beams intersect at an angle of substantially 60°.

6. A particle analyzer as claimed in claim 1 and wherein each of the first and second detection means comprise a lens array, a photodetector and respectively a first and a second optical wavelength filter which allows only light from the first or second radiation beam to reach the respective photodetectors.

7. A particle analyzer as claimed in claim 6 and having means defining an aperture in front of the detectors adapted to restrict the field of view thereof to substantially the virtual measurement space.

8. A particle analyzer as claimed in claim 1, wherein the means for comparing provides an output indicative of particle size.

9. A particle analyzer as claimed in claim 1 and adapted for distinguishing between a particle of ice crystal and a particle comprised of a super-cooled water droplet.

10. A particle analyzer as claimed in claim 1 and adapted for deployment on an aircraft.

11. A particle analyzer as claimed in claim 10 and adapted and arranged to provide an instantaneous indication to an aircrewman of the nature of particles in the vicinity of the aircraft.

12. A method of particle analysis for analyzing at least one of the shape and size of a particle, said method comprising the steps of:

directing a first beam of radiation having a first wavelength at a second beam of radiation having a second wavelength, the two wavelengths being different, the intersection of the two beams form a virtual measurement space through which said particle passes;

detecting with an array of detectors at a plurality of locations radiation of said first wavelengths scattered by said particle and generating first radiation signals;

detecting with a second detection means radiation of said second wavelength scattered by said particle and generating electrical signals corresponding thereto, and processing said first and second radiation signals for coincidence indicating that radiation was scattered from a particle located in said virtual measurement space, and, analyzing and comparing said first radiation signals with data from particles of known shape to derive at least one of shape and size data relating to said particle.

13. A method as claimed in claim 12 and adapted for discriminating between water droplets and ice crystals.

* * * * *